(12) United States Patent
Kumbakonam (10) Patent No.: US 10,803,769 B2
(45) Date of Patent: Oct. 13, 2020

(54) SYSTEM AND METHOD FOR GENERATING A RECIPE PLAYER

(71) Applicant: Sundaresan Natarajan Kumbakonam, Bangalore (IN)

(72) Inventor: Sundaresan Natarajan Kumbakonam, Bangalore (IN)

( * ) Notice: Subject to any disclaimer, the term of this patent is extended or adjusted under 35 U.S.C. 154(b) by 286 days.

(21) Appl. No.: 15/796,651

(22) Filed: Oct. 27, 2017

(65) Prior Publication Data

US 2019/0130786 A1    May 2, 2019

(51) Int. Cl.
| | | |
|---|---|---|
| *G09B 19/00* | (2006.01) | |
| *G06Q 50/00* | (2012.01) | |
| *G09B 5/02* | (2006.01) | |
| *G09B 5/04* | (2006.01) | |
| *G09B 5/12* | (2006.01) | |
| *G09B 5/06* | (2006.01) | |
| *G06F 3/0481* | (2013.01) | |
| *G06F 3/0482* | (2013.01) | |
| *G06Q 30/06* | (2012.01) | |
| *G16H 20/60* | (2018.01) | |
| *A23L 5/10* | (2016.01) | |
| *G01N 33/02* | (2006.01) | |

(52) U.S. Cl.
CPC ....... *G09B 19/0092* (2013.01); *G06F 3/0481* (2013.01); *G06Q 50/01* (2013.01); *G09B 5/02* (2013.01); *G09B 5/04* (2013.01); *G09B 5/065* (2013.01); *G09B 5/12* (2013.01); *G09B 5/125* (2013.01); *G09B 19/0038* (2013.01); *A23L 5/10* (2016.08); *G01N 33/02* (2013.01); *G06F 3/0482* (2013.01); *G06Q 30/0633* (2013.01); *G16H 20/60* (2018.01)

(58) Field of Classification Search
CPC ........ G09B 19/0092; G09B 5/02; G09B 5/04; G09B 5/065; G09B 5/12; G09B 5/125; G09B 19/0038; G16H 20/60; G01N 33/02; A23L 5/10; G06F 3/0482; G06F 3/0481; G06Q 50/01; G06Q 30/0633
See application file for complete search history.

(56) References Cited

U.S. PATENT DOCUMENTS

| | | | | |
|---|---|---|---|---|
| 2012/0136864 A1* | 5/2012 | Ochtel | ............... | G06Q 30/0633 707/738 |
| 2013/0052616 A1* | 2/2013 | Silverstein | ......... | G09B 19/0092 434/127 |
| 2013/0149678 A1* | 6/2013 | Tokuda | ................. | A47J 36/321 434/127 |
| 2013/0149679 A1* | 6/2013 | Tokuda | ............. | G09B 19/0092 434/127 |
| 2013/0171304 A1 | 7/2013 | Huntley | | |

(Continued)

*Primary Examiner* — Jack Yip
(74) *Attorney, Agent, or Firm* — Ellenoff Grossman & Schole LLP; James M. Smedley; Alex Korona (57) ABSTRACT

A system and method of generating a recipe player. The recipe player includes a recipe module that receives a recipe as input data and generates an ingredients file and a cooking instructions file therefrom. The recipe module also generates a graphical user interface for presenting cooking instructions and recipe information to a user. The recipe module includes an ingredients quantity engine configured to calculate an amount of each ingredient needed to cook a selected recipe based on serving size.

20 Claims, 9 Drawing Sheets

(56) References Cited

U.S. PATENT DOCUMENTS

| | | | |
|---|---|---|---|
| 2013/0224694 A1* | 8/2013 | Moore | G16H 20/60 434/127 |
| 2014/0080102 A1* | 3/2014 | Krishna | G09B 19/0092 434/127 |
| 2014/0158753 A1 | 6/2014 | Sisselman | |
| 2014/0272817 A1* | 9/2014 | Park | G09B 5/02 434/127 |
| 2015/0324828 A1* | 11/2015 | Ouimet | G06Q 30/0222 705/14.23 |
| 2016/0081515 A1 | 3/2016 | Aboujassoum | |
| 2016/0286837 A1 | 10/2016 | Yu | |
| 2017/0316488 A1* | 11/2017 | Kremen | G09B 5/06 |
| 2017/0316489 A1* | 11/2017 | Sampara | G06Q 30/0631 |
| 2017/0345185 A1* | 11/2017 | Byron | G06Q 50/12 |
| 2018/0096411 A1* | 4/2018 | Charles | G06Q 30/0633 |
| 2018/0101608 A1* | 4/2018 | Thysell | G06F 16/338 |

* cited by examiner

SYSTEM AND METHOD FOR GENERATING A RECIPE PLAYER

FIELD OF THE INVENTION

The present invention generally relates to an interactive electronic recipe player.

BACKGROUND

Cooking is an ancient practice that many have tried to master, but few have succeeded. People often try to replicate recipes of proven chefs or cooks, or even Grandma's recipes, but there are many challenges to reproducing the taste and satisfaction associated with the original recipe. For instance, the novice cook may leave out key ingredients, or use an incorrect quantity of an ingredient. Another potential problem is cooking the meal at the wrong temperature or for the wrong amount of time. Still other problems occur with trying to read through a long list of ingredients and procedures while actively engaged in the cooking process. This often leads to frustration on the part of the cook and suboptimal results. Disastrous results can manifest if the meal is inedible and hours of work and ingredients are wasted.

Advances in technology in the form of the Internet, wireless communications, and easy-to-use portable electronic devices have made recipe creation and usage easier. A novice cook now has access to countless recipes which he or she can access on the Internet using their desktop, laptop, or mobile device. The recipes are often posted on cooking related websites or blogs and include lists of ingredients, quantities of each ingredient that depend on number of servings, and the steps required to cook the meal or entree. Although these technologies have made the cooking process easier by providing easy access to recipes, there are still problems such as trying to scroll through cooking steps while engaged in the cooking process. This is especially problematic when the cook's hands are dirty or sticky from touching the ingredients and some portion of the ingredients are transferred onto the computing device. This can lead to keys or buttons getting jammed with cooking debris, or may even cause irreparable damage to the computing device by, for example, accidentally spilling liquids on the device. A cook trying to avoid getting a device dirty may accidentally drop the device, potentially causing damage and leading to more frustration.

Another problem encountered by would be cooks is the lack of consistency between recipe websites. Some recipe sites provide videos of how to prepare a particular meal, but do not provide an easy to view ingredient list, as the ingredient list is typically only shown for a few seconds at the beginning of the video and is difficult to search and review the list of ingredients. Other sites include easy to view ingredient lists, but lack audio visual content that helps demonstrate how to cook the meal. Even those sites that include audio visual content such as cooking videos vary widely in terms of quality. For example, some videos are low quality and difficult to follow. In other cases, the video producer spends an inordinate amount of time discussing irrelevant issues, possibly for entertainment purposes, rather than focusing on the cooking task, which requires a user to listen to unnecessary commentary on subsequent preparations of the same recipie.

Yet another problem is the lack of reliable ratings for recipes across different websites and blogs. In some cases, poor ratings may be from a disgruntled person who did not follow the recipe correctly. In other cases, the up-votes or "likes" are sometimes for the "cook" or presenter rather than for the dish or the recipe. Many times, ratings are a result of comments left by individuals who never even bothered trying to cook the meal.

Accordingly, there is a need for an easy-to-use, interactive electronic cooking assistant that allows the cook to focus on cooking without the distractions of using buttons, keyboards or touchscreens to find ingredients or scroll through instructions. Moreover, there is a need for a cooking system that has consistent content in the form of ingredient lists, easy-to-follow instructions, multimedia content that suits different types of users, an easily accessible central database of recipes, and a reliable rating system for each recipe.

SUMMARY OF THE INVENTION

Accordingly, it is an object of the present invention to provide a system and method for generating a recipe player that (i) provides a list of ingredients and cooking instructions in both audio (speech) and visual formats, including in the form of images and videos and (ii) receives inputs via a touch or keyboard and also via audio based on if a user is previewing a recipe or actually cooking.

According to an embodiment of the present invention, a system for generating and providing a recipe player that includes a recipe module, comprising computer-executable code stored in non-volatile memory, a processor, and a communications means. The recipe module, processor, and communications means are operably connected and configured to: receive a recipe as input; in the form of text or a web URL and generate an ingredients file and a cooking instructions file; store the ingredients file and cooking instructions file in a recipe folder in a recipe database, along with the associated images or videos for the ingredients or the cooking steps. The recipe module also includes a standard Nutrition Database engine configured to calculate the nutritional information for a single serving of the dish.

The recipe module, processor, and communications means are further configured to generate a graphical user interface (GUI) that includes: a recipe search option configured to allow a user to search for recipes using descriptive terms or key words, the name of the recipe creator, a category of food, or other suitable criteria; and a listing or gallery of recipes organized according to at least one of the following criteria: category of food, calorie count, ingredients, type of meal (including an appetizer, dessert or a main course), cuisine type, geographic area associated with the recipe, excluded ingredients, dietary requirement, health condition, or any combination of these criteria.

The GUI also includes a selectable presentation option that includes the following presentation and input formats: touch or key board, for the preview mode, of text, images and videos and voice input and voice interface, when the cooking mode is on.

The GUI also includes a sharing option wherein a user can designate one or more other users to view or receive access to a selected recipe link.

The recipe player GUI includes a request for the number of individual servings desired and immediately scales and displays the right quantity for each ingredient and the appropriate time needed to cook a larger or smaller quantity.

The GUI also includes a ratings interface configured to prompt the user to rate the recipe after the user has prepared or tried to prepare a meal according to the recipe, thus ensuring that a rating cannot be given without actually preparing and spending time with the dish and displaying an image of the actual dish cooked. After verification that a recipe has been attempted, GUI can then present a rating for each recipe based on one or more ratings received through the ratings interface.

According to an embodiment of the present invention, a method for generating a recipe player, the method includes: receiving a recipe as input; generating an ingredients file and a cooking instructions file; and storing the ingredients file and cooking instructions file in a recipe folder in a recipe database. The recipe module includes an ingredients quantity engine configured to calculate an amount of ingredients to use for cooking a meal based on an inputted serving size.

The method also includes the step of generating a graphical user interface (GUI) that includes: a recipe search option configured to allow a user to search for recipes using descriptive terms or key words, the name of the recipe creator, a category of food, or any other suitable criteria; and a listing or gallery of recipes organized according to at least one of the following criteria: category of food, calorie count, ingredients, type of meal including breakfast, lunch or dinner, cuisine type, geographic area associated with the recipe, excluded ingredients, dietary requirement, health condition, or any combination of these criteria.

The GUI includes a selectable presentation option that includes the following formats: text only, audio-visual video presentation, audio only, or audio-visual animation. The instructions are presented to a user according to the selected presentation option.

The GUI includes a sharing option where a user can designate one or more other users to receive access to a selected recipe file.

The GUI includes a ratings interface configured to prompt the user to rate the recipe after the user has prepared or tried to prepare a meal according to the recipe. The method includes presenting a rating for each recipe based on one or more ratings received through the ratings interface.

The foregoing summary of the present invention with the preferred embodiments should not be construed to limit the scope of the invention. It should be understood and obvious to one skilled in the art that the embodiments of the invention thus described may be further modified without departing from the spirit and scope of the invention.

BRIEF DESCRIPTION OF THE DRAWINGS

Like reference symbols in the various drawings indicate like elements.

DETAILED DESCRIPTION OF ILLUSTRATIVE EMBODIMENTS

Accordingly, it is an object of the present invention to provide a system and method for generating a recipe player and sharing recipes with others.

Figure 1:
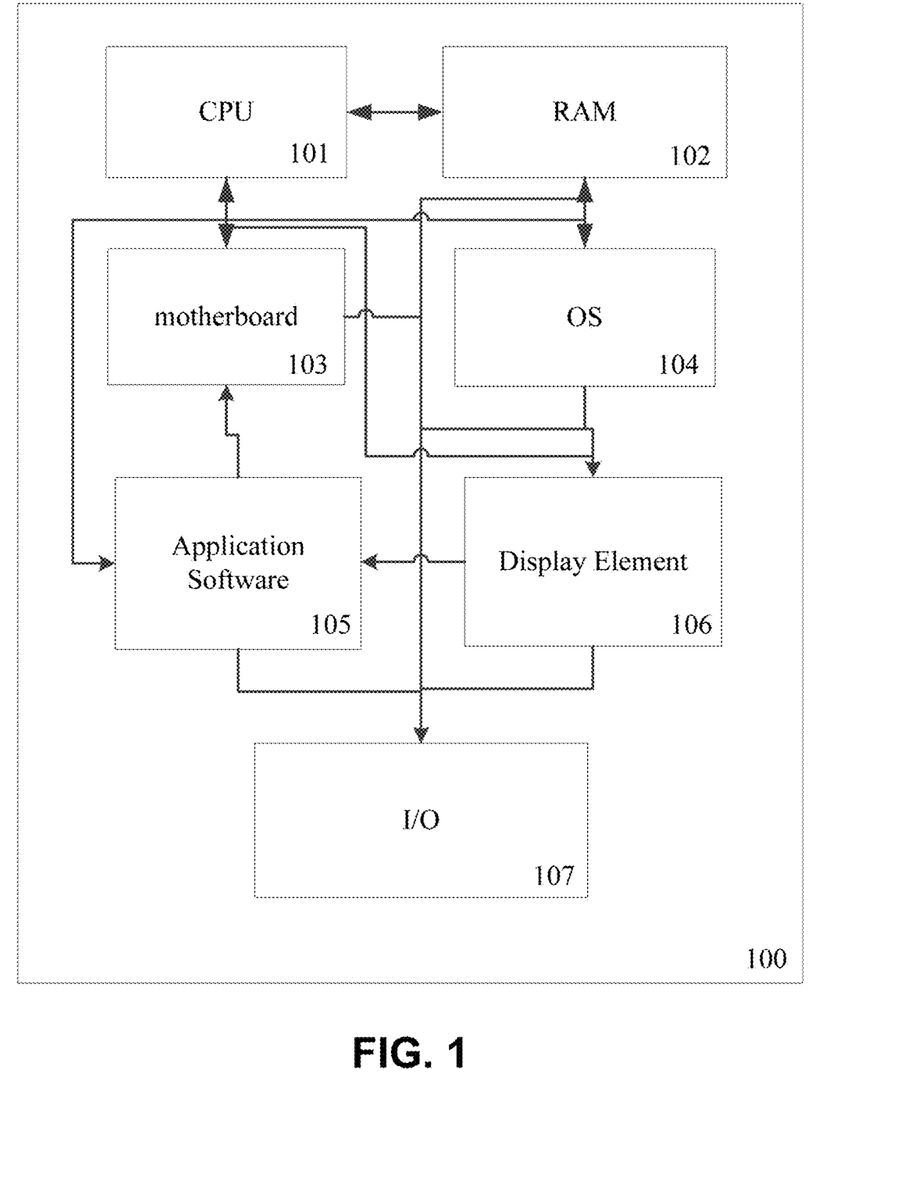
FIG. 1 is a schematic view of a process flow, in accordance with embodiments of the present invention.

According to an embodiment of the present invention, the system and method is accomplished through the use of one or more computing devices. As shown in FIG. 1, one of ordinary skill in the art would appreciate that a computing device 100 appropriate for use with embodiments of the present application may generally be comprised of one or more of a Central processing Unit (CPU) 101, Random Access Memory (RAM) 102, a storage medium (e.g., hard disk drive, solid state drive, flash memory, cloud storage) 103, an operating system (OS) 104, one or more application software 105, display element 106 and one or more input/output devices/means 107. Examples of computing devices usable with embodiments of the present invention include, but are not limited to, personal computers, smart phones, laptops, mobile computing devices and tablet PCs and servers. One of ordinary skill in the art would understand that any number of computing devices could be used, and embodiments of the present invention are contemplated for use with any computing device.

In an exemplary embodiment according to the present invention, data may be provided to the system, stored by the system and provided by the system to users of the system across local area networks (LANs) (e.g., office networks, home networks) or wide area networks (WANs) (e.g., the Internet). In accordance with the previous embodiment, the system may be comprised of numerous servers communicatively connected across one or more LANs and/or WANs. One of ordinary skill in the art would appreciate that there are numerous manners in which the system could be configured and embodiments of the present invention are contemplated for use with any configuration.

In general, the system and methods provided herein may be consumed by a user of a computing device whether connected to a network or not. According to an embodiment of the present invention, some of the applications of the present invention may not be accessible when not connected to a network, however a user may be able to compose data offline that will be consumed by the system when the user is later connected to a network.

Figure 2:
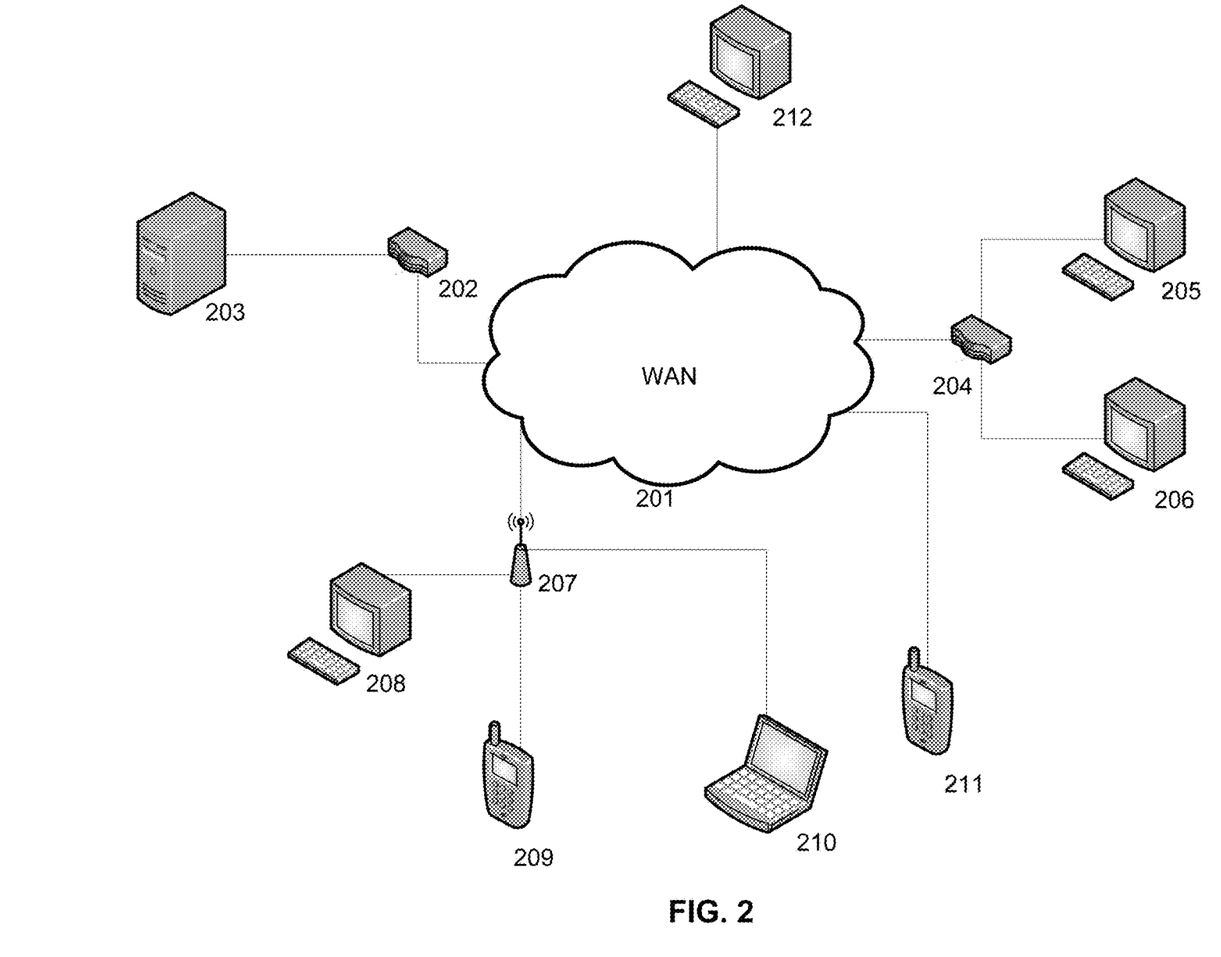
FIG. 2 is a schematic view of a computing device, in accordance with embodiments of the present invention.

Referring to FIG. 2, a schematic overview of a system in accordance with an embodiment of the present invention is shown. The system is comprised of one or more application servers 203 for electronically storing information used by the system. Applications in the server 203 may retrieve and manipulate information in storage devices and exchange information through a WAN 201 (e.g., the Internet). Applications in server 203 may also be used to manipulate information stored remotely and process and analyze data stored remotely across a WAN 201 (e.g., the Internet).

According to an exemplary embodiment, as shown in FIG. 2, exchange of information through the WAN 201 or other network may occur through one or more high speed connections. In some cases, high speed connections may be over-the-air (OTA), passed through networked systems, directly connected to one or more WANs 201 or directed through one or more routers 202. Router(s) 202 are completely optional and other embodiments in accordance with the present invention may or may not utilize one or more routers 202. One of ordinary skill in the art would appreciate that there are numerous ways server 203 may connect to WAN 201 for the exchange of information, and embodiments of the present invention are contemplated for use with any method for connecting to networks for the purpose of exchanging information. Further, while this application refers to high speed connections, embodiments of the present invention may be utilized with connections of any speed.

Components of the system may connect to server 203 via WAN 201 or other network in numerous ways. For instance, a component may connect to the system i) through a computing device 212 directly connected to the WAN 201, ii) through a computing device 205, 206 connected to the WAN 201 through a routing device 204, iii) through a computing device 208, 209, 210 connected to a wireless access point 207 or iv) through a computing device 211 via a wireless connection (e.g., CDMA, GMS, 3G, 4G) to the WAN 201. One of ordinary skill in the art would appreciate that there are numerous ways that a component may connect to server 203 via WAN 201 or other network, and embodiments of the present invention are contemplated for use with any method for connecting to server 203 via WAN 201 or other network. Furthermore, server 203 could be comprised of a personal computing device, such as a smartphone, acting as a host for other computing devices to connect to.

Figure 3:
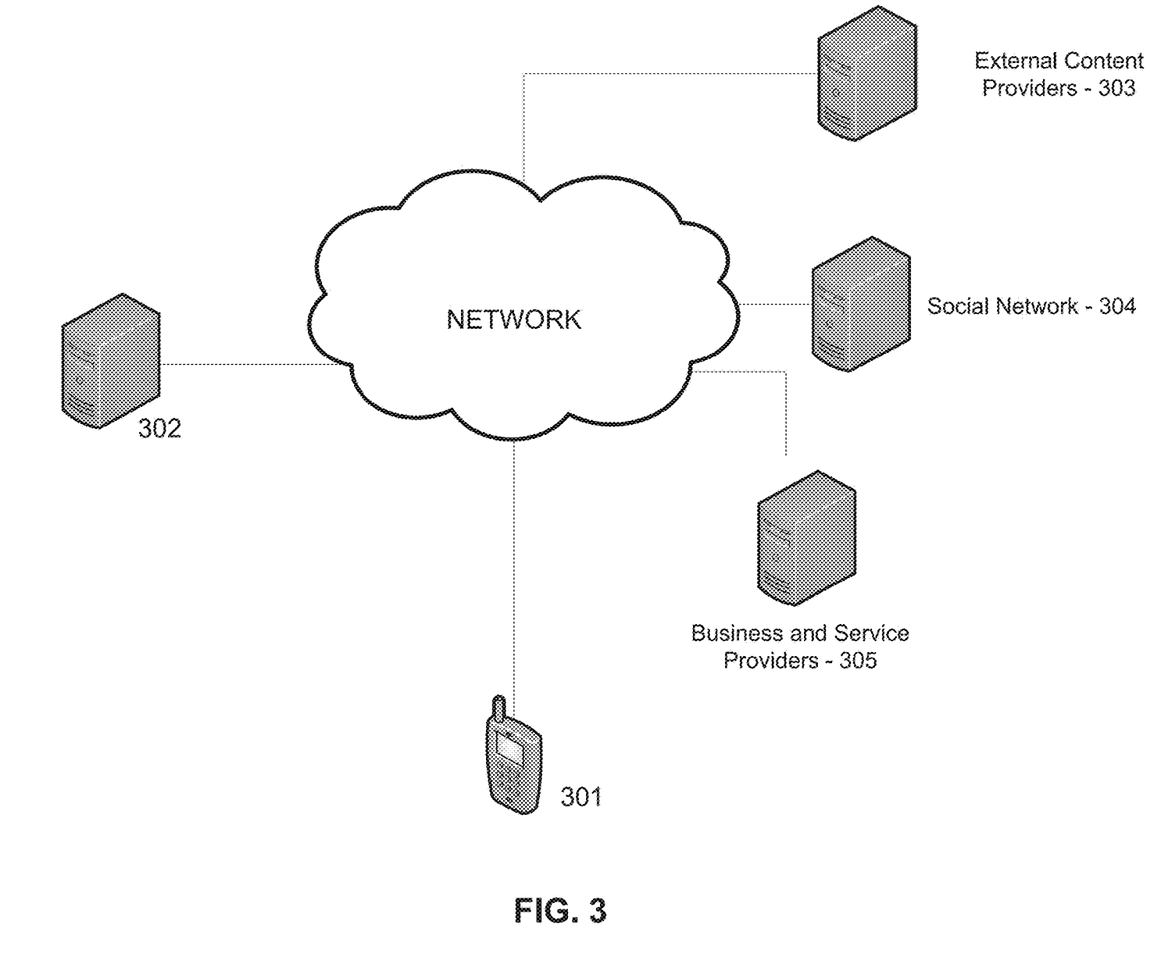
FIG. 3 is a schematic view of a network, in accordance with embodiments of the present invention.

Turning now to FIG. 3, a continued schematic overview of a system in accordance with an embodiment of the present invention is shown. In FIG. 3, the system is shown as it may interact with users and other third party networks or APIs. For instance, a user of a mobile device 301 may be able to connect to application server 302. Application server 302 may be able to enhance or otherwise provide additional services to the user by requesting and receiving information from one or more of an external content provider API/website or other third party system 303, a social network 304, one or more business and service providers 305 or any combination thereof. Additionally, application server 302 may be able to enhance or otherwise provide additional services to an external content provider API/website or other third party system 303, a social network 304, or one or more business and service providers 305 by providing information to those entities that is stored on a database that is connected to the application server 302. One of ordinary skill in the art would appreciate how accessing one or more third-party systems could augment the ability of the system described herein, and embodiments of the present invention are contemplated for use with any third-party system.

According to an embodiment of the present invention, a system for generating a recipe player is provided. The system includes a recipe module that includes computer-executable code stored in non-volatile memory; a processor; and a communications means which are operably connected and are configured to: receive a recipe as input; generate an ingredients file and a cooking instructions file; and store the ingredients file and cooking instructions file in a recipe folder in a recipe database.

The recipe module of the present invention includes an ingredients quantity engine configured to calculate an amount of ingredients to use for cooking a meal based on an inputted serving size.

The recipe module, processor, and communications means are further configured to generate a graphical user interface (GUI) that includes: a recipe search option configured to allow a user to search for recipes using descriptive terms, the name of the recipe creator, a category of food, or any other suitable criteria.

The GUI is further configured to display a listing or gallery of recipes organized according to at least one of the following criteria: category of food, calorie count, ingredients, type of meal including breakfast, lunch or dinner, cuisine type, geographic area associated with the recipe, excluded ingredients, dietary requirement, health condition, or any combination of these criteria. Furthermore, the criteria used to organize the listing or gallery may be used as search criteria in the recipe search option. For example, a user might select a category of food, such as Thai food, from a drop-down menu, when searching for recipes. Or a user might select a health condition, such as diabetic, as a search filter to screen out recipes that might constitute a health risk to the user. One of ordinary skill in the art will recognize that any combination of the above listed criteria can be used to either search for recipes or filter a list/gallery of recipes.

The GUI also includes a selectable presentation option that includes the following formats: text only, audio-visual video presentation, audio only, or audio-visual animation, where the cooking instructions are presented to a user according to the selected presentation option. The audio-visual video, audio-visual animation, and audio only options provide a user a "hands-free" option of watching and/or listening to the recipe cooking instructions without having to physically interact with the device on which the recipe player is playing. These hands-free options are also configured to accept voice commands from a user such as "pause", "rewind", "fast forward", "repeat", "increase volume", "lower volume", "start", "stop", "turn off", etc. One of ordinary skill in the art would recognize that there are many different voice commands that could be included, and the system described is not limited to the specific commands listed above.

The GUI also includes a sharing option where a user can designate one or more other users to view or receive access to a selected recipe file. For example, a user can share a link to a particular recipe which when clicked or selected by a recipient automatically activates a recipe player instance that plays cooking instructions for the specified recipe. Alternatively, the link may take the recipient to a GUI associated with the specified recipe that allows a user to access information about the recipe in a "view mode" or play recipe cooking instructions in a "cook mode" according to a selected presentation format, such as text, audio-visual video, audio-visual animation, or audio only.

The GUI also includes a ratings interface configured to prompt the user to rate the recipe after the user has fully prepared a meal according to the recipe, or tried to prepare the meal. In one embodiment, the GUI requires that a user prepare or try to prepare the meal according to the recipe before the user can rate the recipe. One way the system can track whether a user actually used the recipe to prepare a meal is with a timer that is activated when the user starts a recipe player instance. The system may also activate a video camera to record the user cooking the meal. The video and/or timer can be used in concert to try to verify whether a user engaged in cooking. For example, if a user spends less than a predetermined period using the recipe player then the system does not prompt the user to provide a rating for the recipe. In this way, the system promotes the integrity and authenticity of the ratings by excluding ratings from users who did not actually try to cook a meal by following the recipe. The GUI uses the stored ratings to present a rating for each recipe based on one or more ratings received through the ratings interface.

As mentioned above, the GUI includes one or more interactive modes, such as a "cook mode" in which instructions for cooking a recipe are presented to a user, and a "view mode" in which information about the recipe is presented to a user. In cook mode the user can select from a variety of different presentation options that determine the format of the cooking instructions, such as text, video, animation, or audio only. In view mode, the user can watch videos that provide information about the recipe such as its origins, history, nutritional information, health benefits, where to buy the ingredients, etc. Recipe information can also be presented with text, visual illustrations, audio, and animation. One of ordinary skill in the art would recognize that there are many ways to present information about a recipe and there are many types of information that could be provided beyond what is listed herein.

According to an embodiment of the present invention, the GUI may also include a selectable option to generate a printable shopping list from the the recipe ingredients. The recipe ingredients can also be sent to a user in an e-mail or as a text message. For example, a user using the recipe player application or "app" can select an option to text a shopping list of ingredients to themselves, a spouse, or friend who is shopping for groceries.

The GUI of the present invention may also include a selectable option to upload a video of the user cooking a meal based on one of the recipes in the recipe database. The video can then be added to the recipe folder as a sample video of a user cooking the recipe. In another embodiment, the recipe player automatically activates a video camera on a user's computing device when the user starts playing the cooking instructions in cooking mode. As previously mentioned, the video camera can also be used to verify that the user has started preparing a meal according to a selected recipe for purposes of soliciting a rating from the user. In other words, the system will not prompt the user for a rating unless there is evidence (e.g. a video and/or timer indicating that a preset period has passed since the cooking instructions were started) that the user attempted to follow the recipe. This condition is used to promote the integrity and authenticity of ratings, but in other embodiments this condition may not be required.

According to an embodiment of the present invention, the recipe player app also includes a social media component in which a plurality of users can chat, share recipes, rate each other's recipes, share content related to recipes, and conduct cooking classes. Organizing cooking classes is especially useful since it allows participating users to ask questions during the class.

According to one embodiment, when a user selects a recipe from the list or gallery of recipes, the recipe player app includes an allergy checker function configured to access an allergy database, retrieve any warnings associated with one or more ingredients in the recipe, and present warnings to the user. This allergy checker function can be activated or deactivated by a user as necessary. The allergy database may be a third-party database that is accessed through an application programming interface (API) or an allergy database included as part of the recipe player app. Alternatively, the allergy checker function may automatically perform an Internet search for allergy related information for one or more ingredients instead of, or in addition to, accessing an allergy database. The retrieved allergy information can then be provided to the user.

The GUI of the recipe player may further include a selectable option for editing or deleting a recipe file, such as the ingredients file or cooking instructions file. Similarly, new files, such as videos of users cooking a recipe, may be added to an existing recipe folder. However, editing or deleting a recipe file may be restricted to administrative level users or users with certain credentials.

According to an embodiment of the present invention, the GUI of the recipe player displays a cook time for each recipe. The cook time for a recipe may be derived from an average cook time of all users who used the recipe, or may be a recommended cook time for the recipe. Furthermore, the GUI could display a total cook time for cooking the recipe meal and/or times to complete each step of the cooking process. As previously mentioned, the recipe player app includes a hands-free option in which cooking instructions are presented to the user by audio-visual video, animation, or audio only. In this case, the recipe player may announce how much time the cooking process should take and/or or how long each step of the cooking process should take. In another embodiment, the recipe player provides a countdown for the cooking process and/or cooking steps and generates a warning when the cook time is about to expire or when a user has exceeded the recommended or average time for completing the step or cooking the meal. For example, the cooking instructions may call for placing an item in the oven for 45 minutes at 400 degrees Fahrenheit. The recipe player would then provide a warning when there is 5 minutes left and/or when the 45-minute period has expired.

According to an embodiment of the present invention, a method of generating a recipe player is provided. The method includes: receiving a recipe as input; generating an ingredients file and a cooking instructions file; storing the ingredients file and cooking instructions file in a recipe folder in a recipe database; and calculating an amount of ingredients to use for cooking a meal based on an inputted serving size.

The method of the present invention also includes generating a graphical user interface (GUI) that features: a recipe search option configured to allow a user to search for recipes using descriptive terms or key words, the name of the recipe creator, or a category of food; a listing or gallery of recipes organized according to at least one of the following criteria: category of food, calorie count, ingredients, type of meal including breakfast, lunch or dinner, cuisine type, geographic area associated with the recipe, excluded ingredients, dietary requirement, health condition, or any combination thereof; a selectable presentation option that includes the following formats: text only, audio-visual video presentation, audio only, or audio-visual animation, where cooking instructions are presented to a user according to the selected presentation option; a sharing option where a user can designate one or more other users or recipients to receive access to a selected recipe file and the recipe player GUI; a ratings interface configured to prompt the user to rate the recipe; and presenting a rating for each recipe to the user based on one or more ratings received through said ratings interface.

According to an embodiment of the present invention, the GUI includes a plurality of interactive modes, including a "cook mode" in which instructions for cooking the recipe are presented to a user, and a "view mode" in which information about the recipe is presented to a user. However, fewer or more interactive modes may be included in the GUI and the modes are not limited to those mentioned herein.

As mentioned above, the recipe player GUI may include a selectable option to generate a printable shopping list based on ingredients for a recipe. Furthermore, the GUI includes an option to e-mail or text the shopping list to a user, or other person designated by a user, such as a friend or spouse.

As mentioned above, the GUI may also include a selectable option to upload a video of the user cooking a meal according to a recipe. The video can be stored as a sample cooking video in a recipe folder associated with the recipe in the recipe database. However, permission to upload videos to the recipe folder may be required.

According to an embodiment of the present invention, the method may also include providing a social media component in which a plurality of users can chat, share recipes, rate each other's recipes, share content related to recipes, and conduct cooking classes.

The method of the present invention may also include: accessing an allergy database; retrieving any warnings associated with one or more of said ingredients; and presenting said warnings to the user. Alternatively, the method may automatically perform an Internet search for allergy information for one or more ingredients in the recipe instead of or in addition to accessing an allergy database. The allergy database may be a third-party database accessed through an API or a database included as part of the recipe player. In the latter case, the recipe module accesses a private, proprietary allergy database that is updated regularly.

According to an embodiment of the present invention, the GUI further includes a selectable option for deleting or editing a recipe file, such as the ingredients file or cooking instructions file. However, as mentioned above, deleting or editing a recipe file may be restricted to one or more authorized users such as a user with administrative privileges or other required credentials.

According to an embodiment of the present invention, the GUI may also display an estimated time for preparing a meal according to one of the recipes, and/or an estimated time for completing each step of the cooking process. As mentioned previously, the estimated time may be derived from an average time for all users who prepared the meal, or a recommended time for preparing the meal. The GUI may also provide a countdown and/or a warning that alerts a user when the recommended cook time is about to expire or has been exceeded. For example, the cooking instructions may call for placing an item in the oven for 45 minutes at 400 degrees Fahrenheit. The recipe player would then provide a warning when there is 5 minutes left and/or when the 45-minute period has expired.

Figure 4:
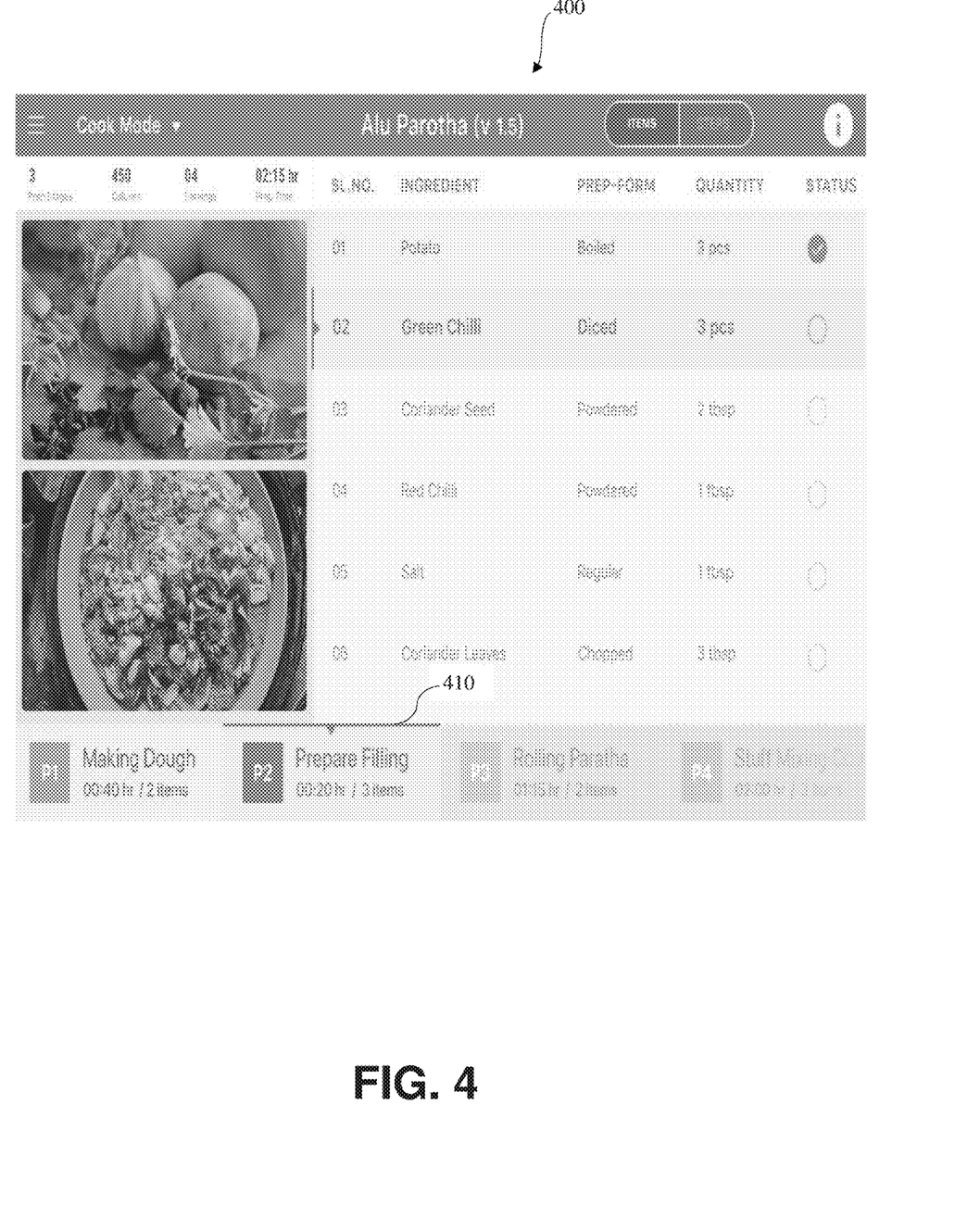
FIG. 4 is an exemplary screen of a graphical user interface according to an embodiment of the present invention.

Turning back to the drawings, FIG. 4 shows an exemplary screen shot 400 of the recipe player GUI in a "cook mode." The GUI screen provided in FIG. 4 is a combination of text and visual illustrations. However, other instructional aids can include video, animation, and audio-only instructions. Furthermore, the GUI is configured to receive voice commands such as "pause", "rewind", "fast forward", "repeat", "start", "stop", "increase volume", "lower volume" or any other suitable command. Commands can also be issued by user with a standard input device such as a mouse, keyboard, stylus, touchscreen, etc.

As further illustrated in FIG. 4, an indicator 410 is used to show the current stage of the cooking process in which the user is engaged. In the exemplary embodiment of FIG. 4, the indicator is displayed over stage P2 (Prepare Filling). Moreover, stages of the cooking process that have not yet commenced may be greyed out, while completed stages and current stages are clearly visible, thus distinguishing between completed or in-progress stages, and stages that have not yet been started. Other indicators may also be displayed in the GUI, such as a calorie indicator, serving size indicator, and prep-time indicator. One of ordinary skill in the art will recognize that many other types of indicators may be displayed in the cook mode GUI and the indicators displayed in FIG. 4 are not exhaustive.

Figure 5:
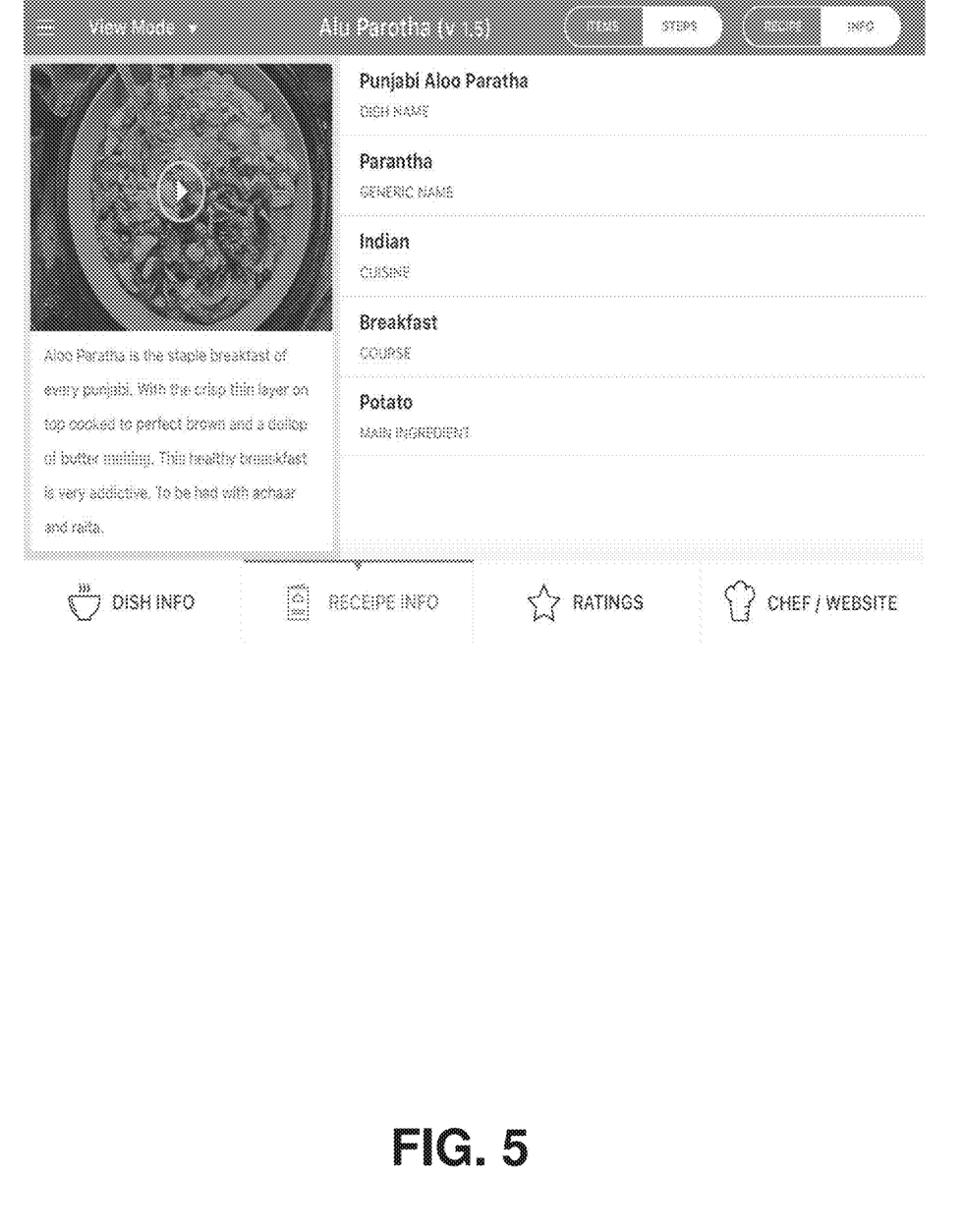
FIG. 5 is another exemplary screen shot of a graphical user interface according to an embodiment of the present invention.
Figure 6:
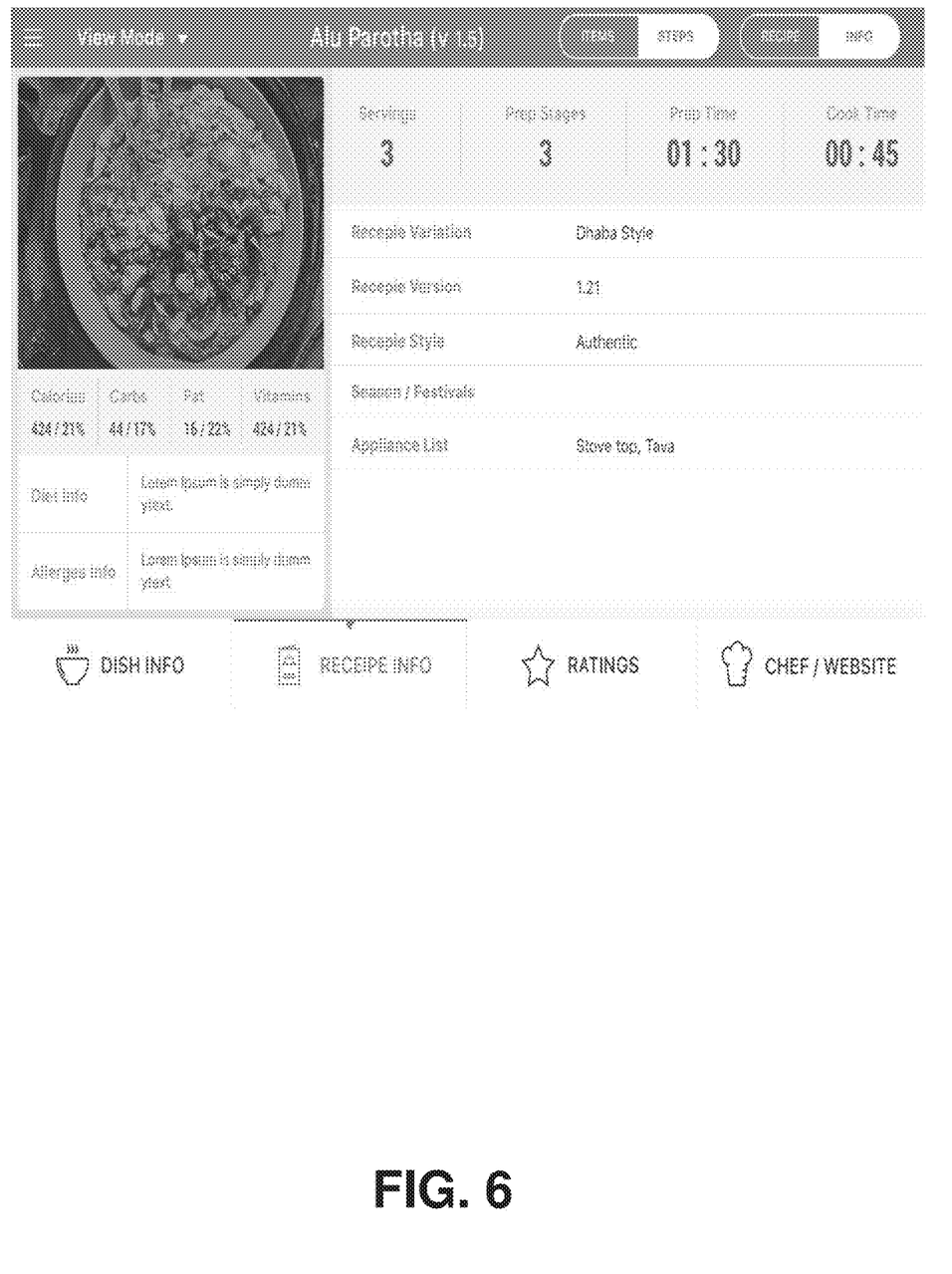
FIG. 6 is another exemplary screen shot of a graphical user interface according to an embodiment of the present invention.
Figure 7:
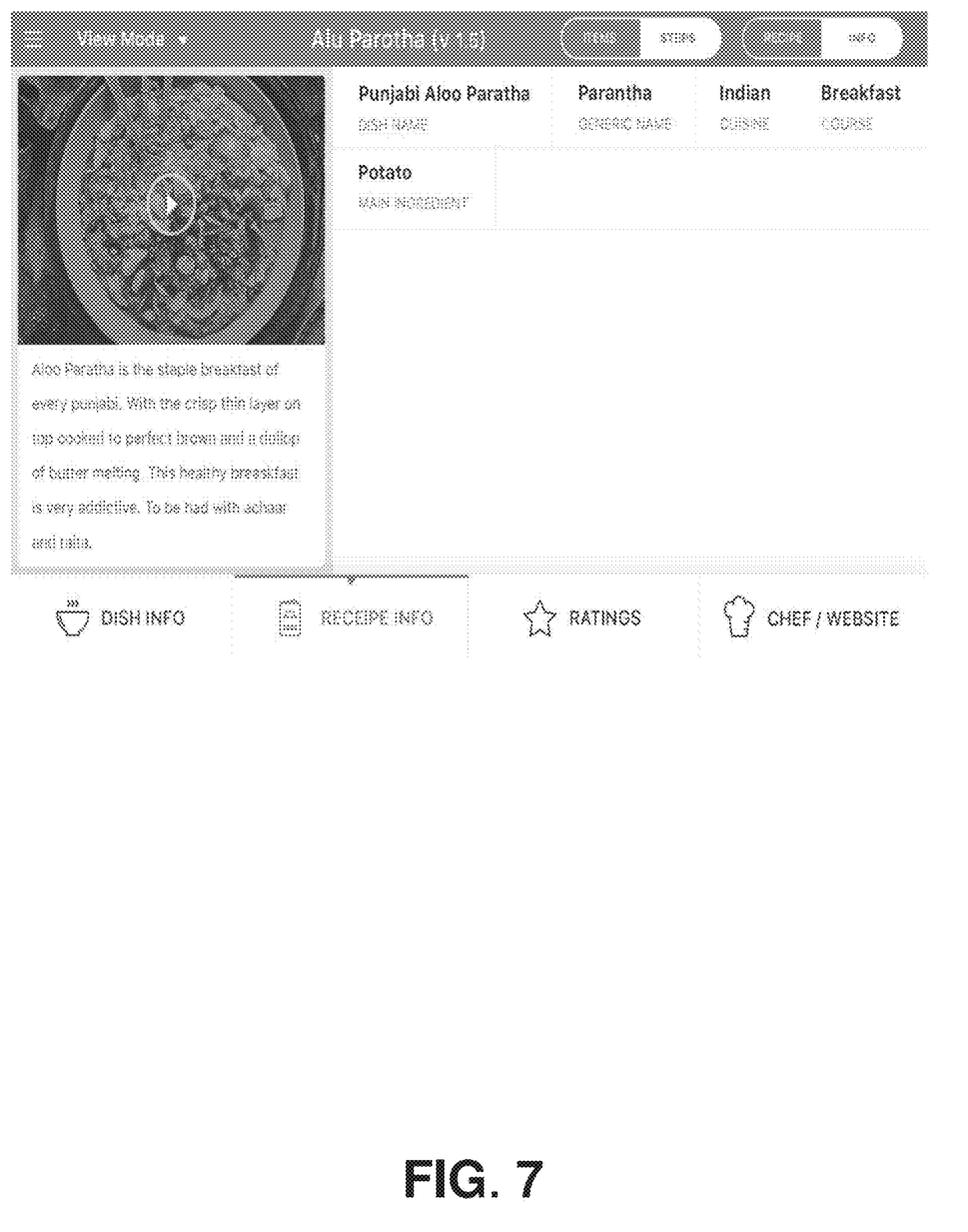
FIG. 7 is another exemplary screen shot of a graphical user interface according to an embodiment of the present invention.

FIGS. 5-7 show screen shots of the recipe player GUI in a "view mode." The GUI screen provided in FIG. 5 shows a video that may be played by a user along with other information about a selected recipe. In addition, the user can check ratings for the selected recipe, dish info, and navigate to a chef website as indicated by the menu of options displayed at the bottom of the screen. Various other indicators may also be displayed, such as cook time and prep time for a meal, serving size, and number of prep stages.

FIGS. 6 and 7 show additional screen shots of the recipe player GUI displaying various information about the recipe, such as nutritional information, diet information, and allergen information. One of ordinary skill in the art will recognize that many other types of information about a recipe may be provided and the GUI screens shown in FIGS. 4-7 are exemplary in nature.

Figure 8:
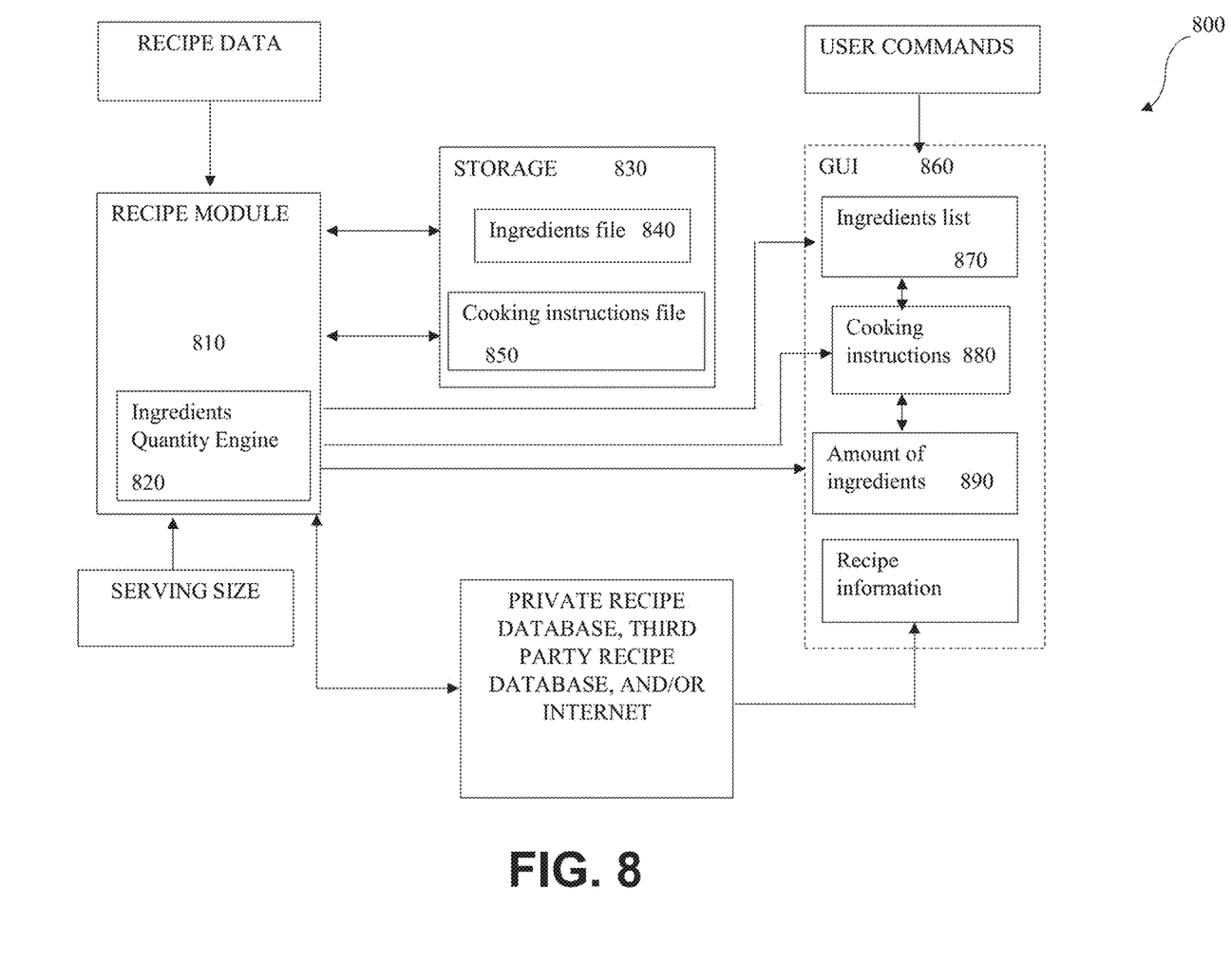
FIG. 8 is a data flow diagram according to an embodiment of the present invention.

FIG. 8 is a data flow diagram showing inputs and outputs of the system, as well as system components (i.e., the recipe module, storage, databases, Internet, GUI) and how data flows between them. As illustrated in FIG. 8, the recipe module 810 accepts a recipe as data input and generates an ingredients file 840 and a cooking instructions file 850 which are stored in, for example, a recipe database. The recipe module 810 includes an ingredients quantity engine 820 that calculates the amount of each ingredient needed for cooking a selected recipe based on serving size. The recipe module further generates a GUI 860 that presents an ingredients list 870, such as a printable shopping list, cooking instructions 880, and amount of each ingredient 890 needed to cook the recipe. The GUI is also configured to present recipe information 900, such as nutritional information, calories, diet information, allergen information, background information, etc. The information provided by the GUI may be acquired from a private database, a third-party database, the Internet, or any combination thereof.

Figure 9:
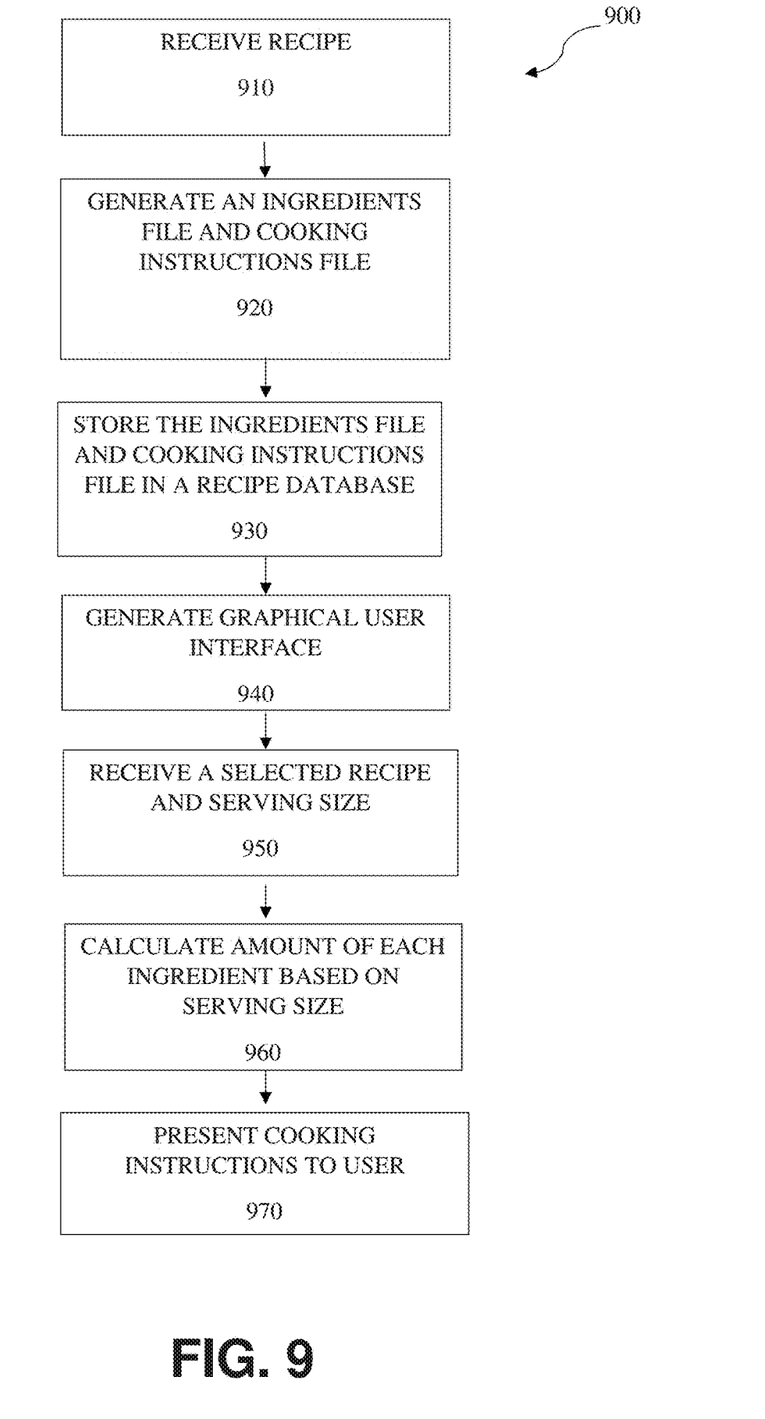
FIG. 9 is a box diagram according to an embodiment of the present invention.

FIG. 9 is a box diagram depicting a method of generating the recipe player of the present invention. One of ordinary skill will appreciate that the steps of the method depicted in FIG. 9 may occur in a different order than what is shown. The computer implemented method 900 starts with receiving a recipe as input 910. Recipe files are then generated in the form of an ingredients file and a cooking instructions file 920. The method further includes storing the recipe files in a recipe database 930.

A GUI is then generated 940 which may include various features, such as: a recipe search option configured to allow a user to search for recipes using descriptive terms or keywords, the name of the recipe creator, or a category of food; a listing of recipes organized according to at least one of the following criteria: category of food, calorie count, ingredients, type of meal including breakfast, lunch or dinner, cuisine type, geographic area associated with the recipe, excluded ingredients, dietary requirement, health condition, or any combination thereof; a selectable presentation option that includes the following formats: text only, audio-visual video presentation, audio only, or audio-visual animation, where the instructions are presented to a user according to the selected presentation option; a sharing option where a user can designate one or more other users to receive access to a selected recipe file and the GUI; and a ratings interface configured to prompt the user to rate the recipe.

A recipe selection and serving size is received 950 through, for example, the GUI and the correct amount of each ingredient is automatically calculated 960 for the selected recipe. Cooking instructions for the selected recipe are then presented 970. As previously discussed, the cooking instructions may be presented in a variety of different formats (e.g. text, video, animation, audio only) depending on the presentation option selected by the user.

The system and method of the invention described herein includes many useful features relating to creating, accessing, searching, editing, publishing, and playing recipes. According to an embodiment of the present invention the recipe database may include: dish information; recipe information; ingredients lists based on the prepatory, cooking and plating stages of the preparation; detailed diet and nutrition information; allergy related information; step-by-step cooking instruction lists; information about the chef; rating information for the recipe; feedback and comments about the recipe; categorized shopping lists based on the ingredients needed; and videos that are auto-playable but which are limited to 10 to 12 seconds in duration.

Recipe sources may include public domain recipes available on the Internet, which can be automatically retrieved and stored in a "Reciplay Format" and can be playable on the player. For purposes of this application Reciplay Format refers to fixed way in which a recipe player app and its associated interface is stored and displayed. A new recipe can be created entirely from scratch in this new format. A new recipe can be created by taking ingredient lists and instructions of cooking phases and can be reused in the new recipe. Any Website with a store of their recipes can be all converted into this new format which can be searched and played. Any new cook or amateur can write and share recipes of high quality using stock images, and built-in Nutrition calculators and unit convertors to make the recipe usable.

Turning again to the recipe database, in one embodiment the database is a global, neutral database that may be used to compare several recipes for a single dish, based different characteristics, such as ratings, calories, time, number of ingredients, comments, number of times cooked, number of reviews, etc. Recipes in the database may be sourced from amateurs, restaurants, chefs, professionals, celebrities, etc. and the recipes may be rated by the user community, using the "TRUE Rating System." The TRUE Rating System refers to a rating system in which a user may not rate a recipe unless the user completes the process of cooking the dish described in the recipe. In other words, a user viewing a recipe in "view mode" is not permitted to rate a recipe. Only a user who has gone through the process of cooking the recipe, as verified by tracking the elapsed time a user spent in "cooking mode" or receiving a photo of the cooked dish, is permitted to rate the recipe. The TRUE Rating System thus promotes recipe ratings that are authentic and reliable.

A detailed search of the recipe database can be accomplished from any location based on several criteria, as discussed above, to quickly retrieve a desired recipe. The recipe database may include one or more recipe collections organized according to cuisine type, geography, dietary requirements, health considerations, spiciness, level of difficulty to prepare, or other criteria. The recipe database of the present invention may be part of a paid market place, such as a subscription based service that provides, for example, professional chef recipes and collections.

According to an embodiment of the present invention, each recipe is easily sharable, like YouTube® videos, by sharing a simple unique Recipe ID. Edits can be made to the recipe by the Chef, a user, or an authorized party, to fine tune a given recipe to one's own liking and experimentation. In addition, in one exemplary embodiment only the latest proven recipe is made available in response to a new search.

According to an embodiment of the invention, a simple search bar is provided in the GUI to quickly search recipes using several tags which are used when recipes are created. Tags may include, but are not limited to: name of the dish; cuisine, course, or main ingredient; chef, author, or recipe website provider; difficulty level; diet/nutrition; and/or rating.

According to an embodiment of the invention, the recipe player app is enabled for both desktop, laptop, tablet, and other mobile device. In a preferred use of the recipe player, the device playing the recipe should be viewed roughly at eye level from the cooking hob, similar to a driver navigation app displayed at eye level.

Moreover, as previously mentioned, the recipe player may be voice enabled and "hands free" and provides easy navigation and accessible screens with relevant grouped information. The recipe player further provides real time quantity changes based on serving size.

In addition to the "cook mode" and "view mode" discussed above, other interactive modes may be provided such as: a preview mode to quickly preview the recipe details; a two cooks mode; a teach mode to try an entirely new dish where the player provides step by step cooking lessons ensuring nothing in missed.

According to an embodiment of the present invention, the recipe player may require an acknowledgment from the user for every command, and keeps track of skipped ingredients to remind the user to add missing ingredients.

According to an embodiment of the present invention, the recipe player provides a more reliable rating by accepting ratings only from users who have followed the recipe and completed the dish. The recipe player may be configured to verify whether a user has completed the dish by analyzing an image of the completed dish and/or tracking the elapsed time during stages of the cooking process. Furthermore, the recipe player apply may allow only one recipe review per user.

According to an embodiment of the present invention, the recipe player includes one or more timer widgets to keep track of cooking times. Furthermore, one or more Bluetooth® scales may be integrated into the recipe player app and may be used to convert liquid quantities to weight and keep track of ingredients and quantities ordered.

According to an embodiment of the present invention, the ingredients are stored as a very detailed database and are defined very accurately, in terms of their names, source form, part form, variety, prep-form as used in the recipe and bought forms as available from the store. This level of classification helps to suggest the exact packaging and order size, for a single recipe or a collection of recipes for a single party or a week. Items may also be classified as per their country of origin, cuisine, category, like produce, fruit, dairy, frozen, seafood, meat, poultry, staples, cereals, spices etc., which helps to make specific focused shopping lists as needed According to an embodiment of the present invention, the recipe player app may be linked to food producer web sites through, for example, an application programming interface (API). This would allow a recipe player user to place orders with one or more vendors, such as an organic food seller, through their respective websites. Moreover, the recipe player is configured to promote just-in-time delivery of needed items by providing access to food supplier websites who commit to providing ordered items in short period of time, such as next day delivery. In addition, the recipe player of the present invention may be configured to transmit a user's required items for a particular recipe to a plurality of vendors who may be filtered or ranked according to price, proximity, delivery speed, rating, or other useful criteria.

Throughout this disclosure and elsewhere, block diagrams and flowchart illustrations depict methods, apparatuses (i.e., systems), and computer program products. Each element of the block diagrams and flowchart illustrations, as well as each respective combination of elements in the block diagrams and flowchart illustrations, illustrates a function of the methods, apparatuses, and computer program products. Any and all such functions ("depicted functions") can be implemented by computer program instructions; by special-purpose, hardware-based computer systems; by combinations of special purpose hardware and computer instructions; by combinations of general purpose hardware and computer instructions; and so on—any and all of which may be generally referred to herein as a "circuit," "module," or "system."

While the foregoing drawings and description set forth functional aspects of the disclosed systems, no particular arrangement of software for implementing these functional aspects should be inferred from these descriptions unless explicitly stated or otherwise clear from the context.

Each element in flowchart illustrations may depict a step, or group of steps, of a computer-implemented method. Further, each step may contain one or more sub-steps. For the purpose of illustration, these steps (as well as any and all other steps identified and described above) are presented in order. It will be understood that an embodiment can contain an alternate order of the steps adapted to a particular application of a technique disclosed herein. All such variations and modifications are intended to fall within the scope of this disclosure. The depiction and description of steps in any particular order is not intended to exclude embodiments having the steps in a different order, unless required by a particular application, explicitly stated, or otherwise clear from the context.

Traditionally, a computer program consists of a finite sequence of computational instructions or program instructions. It will be appreciated that a programmable apparatus (i.e., computing device) can receive such a computer program and, by processing the computational instructions thereof, produce a further technical effect.

A programmable apparatus includes one or more microprocessors, microcontrollers, embedded microcontrollers, programmable digital signal processors, programmable devices, programmable gate arrays, programmable array logic, memory devices, application specific integrated circuits, or the like, which can be suitably employed or configured to process computer program instructions, execute computer logic, store computer data, and so on. Throughout this disclosure and elsewhere a computer can include any and all suitable combinations of at least one general purpose computer, special-purpose computer, programmable data processing apparatus, processor, processor architecture, and so on.

It will be understood that a computer can include a computer-readable storage medium and that this medium may be internal or external, removable and replaceable, or fixed. It will also be understood that a computer can include a Basic Input/Output System (BIOS), firmware, an operating system, a database, or the like that can include, interface with, or support the software and hardware described herein.

Embodiments of the system as described herein are not limited to applications involving conventional computer programs or programmable apparatuses that run them. It is contemplated, for example, that embodiments of the invention as claimed herein could include an optical computer, quantum computer, analog computer, or the like.

Regardless of the type of computer program or computer involved, a computer program can be loaded onto a computer to produce a particular machine that can perform any and all of the depicted functions. This particular machine provides a means for carrying out any and all of the depicted functions.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

According to an embodiment of the present invention, a data store may be comprised of one or more of a database, file storage system, relational data storage system or any other data system or structure configured to store data, preferably in a relational manner. In a preferred embodiment of the present invention, the data store may be a relational database, working in conjunction with a relational database management system (RDBMS) for receiving, processing and storing data. In the preferred embodiment, the data store may comprise one or more databases for storing information related to the processing of moving information and estimate information as well one or more databases configured for storage and retrieval of moving information and estimate information.

Computer program instructions can be stored in a computer-readable memory capable of directing a computer or other programmable data processing apparatus to function in a particular manner. The instructions stored in the computer-readable memory constitute an article of manufacture including computer-readable instructions for implementing any and all of the depicted functions.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

The elements depicted in flowchart illustrations and block diagrams throughout the figures imply logical boundaries between the elements. However, according to software or hardware engineering practices, the depicted elements and the functions thereof may be implemented as parts of a monolithic software structure, as standalone software modules, or as modules that employ external routines, code, services, and so forth, or any combination of these. All such implementations are within the scope of the present disclosure.

In view of the foregoing, it will now be appreciated that elements of the block diagrams and flowchart illustrations support combinations of means for performing the specified functions, combinations of steps for performing the specified functions, program instruction means for performing the specified functions, and so on.

It will be appreciated that computer program instructions may include computer executable code. A variety of languages for expressing computer program instructions are possible, including without limitation C, C++, Java, JavaScript, assembly language, Lisp, HTML, and so on. Such languages may include assembly languages, hardware description languages, database programming languages, functional programming languages, imperative programming languages, and so on. In some embodiments, computer program instructions can be stored, compiled, or interpreted to run on a computer, a programmable data processing apparatus, a heterogeneous combination of processors or processor architectures, and so on. Without limitation, embodiments of the system as described herein can take the form of web-based computer software, which includes client/server software, software-as-a-service, peer-to-peer software, or the like.

In some embodiments, a computer enables execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. The thread can spawn other threads, which can themselves have assigned priorities associated with them. In some embodiments, a computer can process these threads based on priority or any other order based on instructions provided in the program code.

Unless explicitly stated or otherwise clear from the context, the verbs "execute" and "process" are used interchangeably to indicate execute, process, interpret, compile, assemble, link, load, any and all combinations of the foregoing, or the like. Therefore, embodiments that execute or process computer program instructions, computer-executable code, or the like can suitably act upon the instructions or code in any and all of the ways just described.

The functions and operations presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will be apparent to those of skill in the art, along with equivalent variations. In addition, embodiments of the invention are not described with reference to any particular programming language. It is appreciated that a variety of programming languages may be used to implement the present teachings as described herein, and any references to specific languages are provided for disclosure of enablement and best mode of embodiments of the invention. Embodiments of the invention are well suited to a wide variety of computer network systems over numerous topologies. Within this field, the configuration and management of large networks include storage devices and computers that are communicatively coupled to dissimilar computers and storage devices over a network, such as the Internet.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

What is claimed is:

1. A system for generating a recipe player, the system comprising:
 a recipe module, comprising computer-executable code stored in non-volatile memory;
 a processor; and
 a communications means, wherein said recipe module, said processor, and said communications means are operably connected and are configured to:
 receive a recipe as input;
 generate an ingredients file and a cooking instructions file;
 store the ingredients file and the cooking instructions file in a recipe database;
 wherein said recipe module further includes an ingredients quantity engine configured to calculate an amount of ingredients to use for cooking a meal based on an inputted serving size;
 generate a graphical user interface (GUI) that includes:
 a recipe search option configured to allow a user to search for recipes using descriptive terms or keywords, the name of the recipe creator, a category of food, and a health condition or dietary requirement,
 wherein the search option is configured to accept a specific health condition as a search filter to screen out recipes that constitute a health risk to the user, said health condition being diabetes;
 a listing or gallery of recipes organized according to the following criteria:
 category of food, calorie count, ingredients, type of meal including breakfast, lunch or dinner, cuisine type, geographic area associated with the recipe, excluded ingredients, dietary requirement, and health condition;
 a selectable presentation option for cooking instructions that includes the following formats: text only, audio-visual video presentation, audio only, or audio-visual animation, wherein said cooking instructions are presented to a user according to the selected presentation option;
 a sharing option wherein a user can designate one or more other users to receive access to a selected recipe file and the GUI;
 a ratings interface configured to prompt the user to rate the recipe only after a user uses or tires to use the recipe to prepare a meal,
 wherein use or attempted use of the recipe is verified by the combination of a video camera and a timer, wherein the video camera is activated to record the user cooking the meal and the timer is activated when the user starts a recipe player instance, wherein the user must spend a predetermined amount of time using the recipe, as measured by the timer, before the use is prompted to provide a rating:

receive a recipe selection from a user for cooking;

receive an inputted serving size;

calculate and display an amount of each ingredient needed to cook the selected recipe; and present the user with cooking instructions for the selected recipe, wherein an acknowledgment from the user is required for every instruction.

2. The system of claim 1, wherein said GUI further comprises a plurality of interactive modes, including a "cook mode" in which instructions for cooking the recipe are presented to a user, and a "view mode" in which information about the recipe is presented to a user.

3. The system of claim 1, wherein said GUI further comprises a selectable option to generate a printable shopping list based on said ingredients.

4. The system of claim 1, wherein said GUI further comprises a selectable option to upload a video of the user cooking a meal based on one of the recipes in the recipe database.

5. The system of claim 1, further comprising a social media component, wherein a plurality of users can chat, share recipes, rate each other's recipes, share content related to recipes, and conduct cooking classes.

6. The system of claim 1, wherein said recipe module, said processor, and said communications means are operably connected and are further configured to:

access an allergy database;

retrieve any warnings associated with one or more of said ingredients; and present said warnings to the user.

7. The system of claim 1, wherein said GUI further comprises a selectable option for editing the recipe file.

8. The system of claim 1, wherein said GUI further comprises a selectable option for deleting the recipe file.

9. The system of claim 1, wherein said recipe module, said processor, and said communications means are further configured to present a rating for the selected recipe.

10. The system of claim 1, wherein said GUI displays a countdown timer for each cooking step and generates a warning when time is about to expire for completing the cooking step.

11. The system of claim 1, wherein said GUI displays an indicator used to show the current stage of the cooking process in which the user is engaged.

12. A method of generating a recipe player, the method comprising:

receiving a recipe as input;

generating an ingredients file and a cooking instructions file;

storing the ingredients file and the cooking instructions file in a recipe folder in a recipe database;

generating a graphical user interface (GUI) that includes:

a recipe search option configured to allow a user to search for recipes using descriptive terms or keywords, the name of the recipe creator, a category of food, and a health condition or dietary requirement, wherein the search option is configured to accept a specific health condition as a search filter to screen out recipes that condition a health risk to the user, said health condition being diabetes;

a listing of recipes organized according to the following criteria: category of food, calorie count, ingredients, type of meal including breakfast, lunch or dinner, cuisine type, geographic area associated with the recipe, excluded ingredients, dietary requirement, and health condition;

a selectable presentation option for cooking instructions that includes the following formats: text only, audio-visual video presentation, audio only, or audio-visual animation, wherein said cooking instructions are presented to a user according to the selected presentation option;

a sharing option wherein a user can designate one or more other users to receive access to a selected recipe file and the GUI;

a ratings interface configured to prompt the user to rate the recipe only after a user uses or tries to use the recipe to prepare a meal, wherein use or attempted use of the recipe is verified by the combination of a video camera and a timer, wherein the video camera is activated to record the user cooking the meal and the timer is activated when the user starts a recipe player instance, wherein the user must spend a predetermined amount of time using the recipe, as measured by the timer, before the user is prompted to provide a rating; receiving a recipe selection from a user for cooking a meal;

receiving an inputted serving size;

calculating and displaying an amount of each ingredient needed to cook the selected recipe;

presenting the user with cooking instructions for the selected recipe, wherein an acknowledgment from the user is required for every instruction.

13. The method of claim 12, wherein said GUI further comprises a plurality of interactive modes, including a "cook mode" in which instructions for cooking the recipe are presented to a user, and a "view mode" in which information about the recipe is presented to a user.

14. The method of claim 12, wherein said GUI further comprises a selectable option to generate a printable shopping list based on said ingredients.

15. The method of claim 12, wherein said GUI further comprises a selectable option to upload a video of the user cooking a meal based on one of the recipes in the recipe database.

16. The method of claim 12, further comprising providing a social media component in which a plurality of users can chat, share recipes, rate each other's recipes, share content related to recipes, and conduct cooking classes.

17. The method of claim 12 further comprising:

accessing an allergy database;

retrieving any warnings associated with one or more of said ingredients; and presenting said warnings to the user.

18. The method of claim 12, wherein said GUI further comprises a selectable option for editing a recipe file.

19. The system of claim 12, wherein said GUI further comprises a selectable option for deleting a recipe file.

20. The method of claim 12, further comprising presenting a rating for the selected recipe.

* * * * *